No. 1033.

E. W. Goodale's Paper Bag Machine.

6 Sheets-Sheet 1

Reissued Sept. 4. 1860

No. 1033 E. W. Goodale's Paper Bag Machine.

Reissued Sept. 14, 1860

No. 1,033.

E. W. Goodale's Paper Bag Machine. Reissued Sept. 4. 1860.

6 Sheets, Sheet 3.

No. 1,033.
E. W. Goodale's Paper Bag Machine. Reissued Sept. 4. 1860.
6 Sheets - Sheet 4.
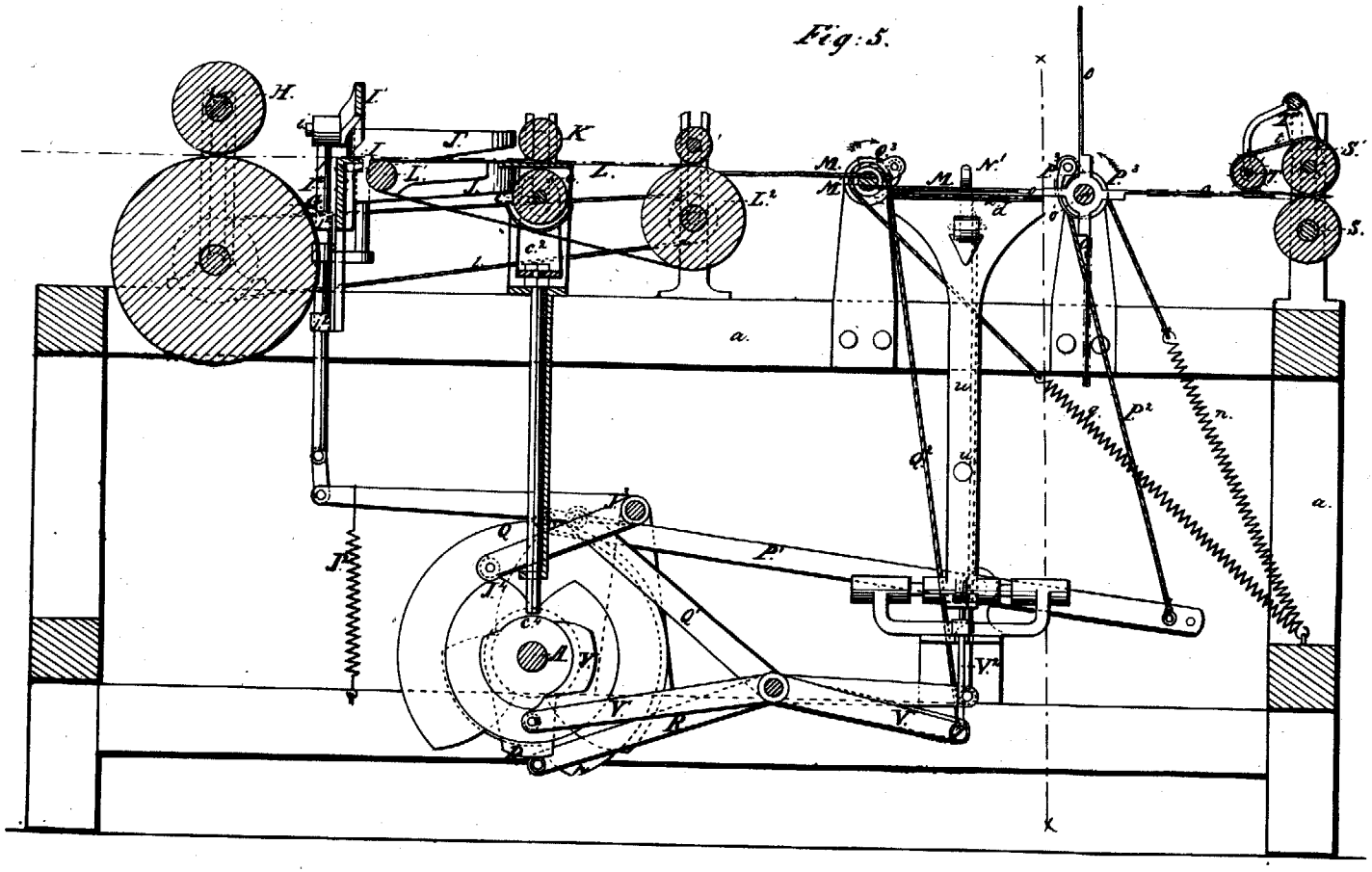

No. 1,033.
E. W. Goodale's Paper Bag Machine.
Reissued Sept. 4. 1860.
6 Sheets, Sheet 5.
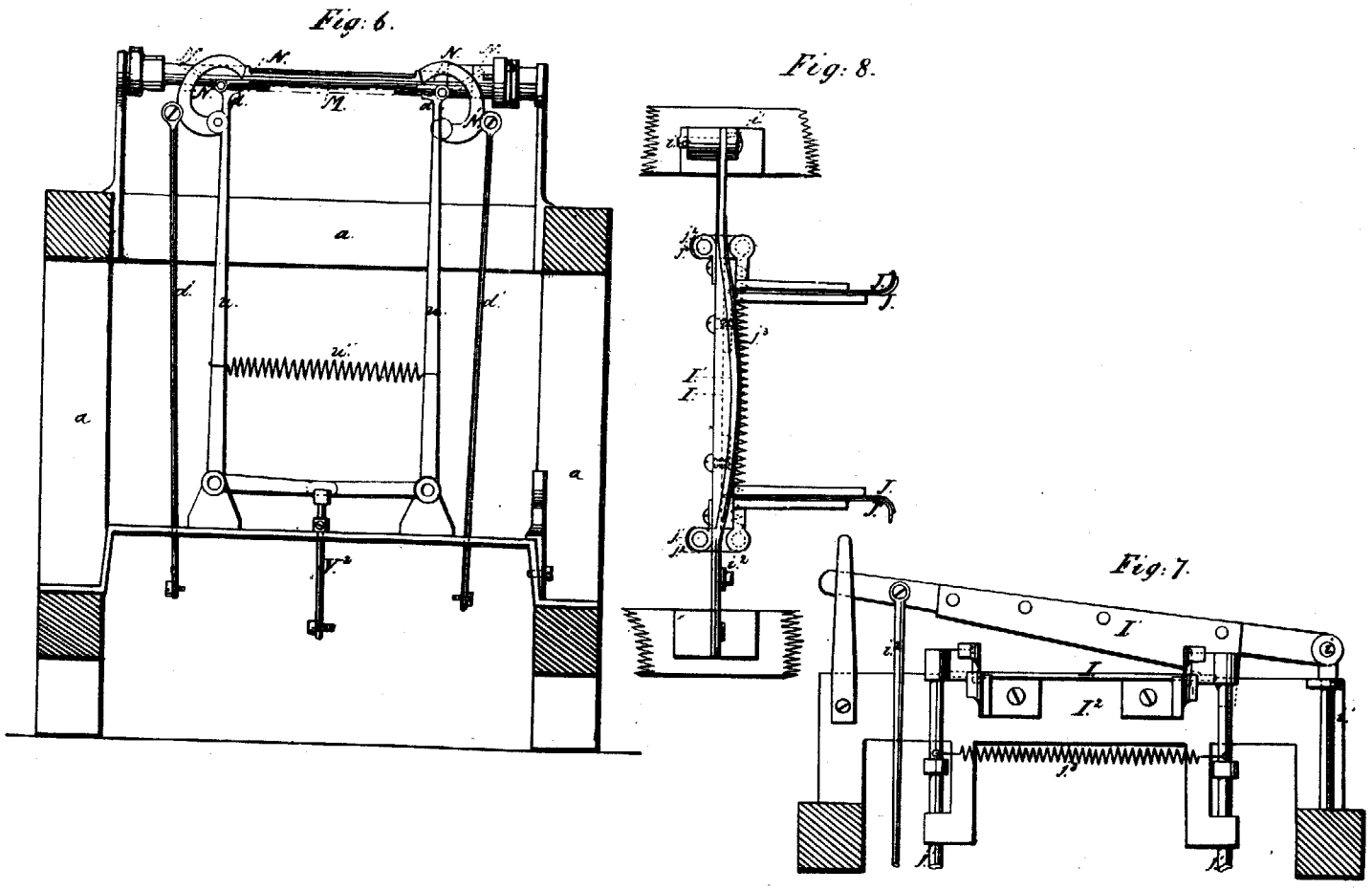

No. 1,033. E. W. Goodale's Paper Bag Machine

Reissued Sept. 4. 1860.

6 Sheets - Sheet 6.

Witnesses.
J. W. Coombs
R. S. Spence.

Inventor.
E. W. Goodale
per Munn & Co
Attorneys.

UNITED STATES PATENT OFFICE.

E. W. GOODALE, OF CLINTON, MASSACHUSETTS.

MACHINE FOR MAKING PAPER BAGS.

Specification forming part of Letters Patent No. 12,945, dated May 29, 1855; Reissue No. 1,033, dated September 4, 1860.

*To all whom it may concern:*

Be it known that I, E. W. GOODALE, of Clinton, in the county of Worcester and State of Massachusetts, have invented certain new and useful Improvements in Machinery for Making Bags of Paper or other Material; and I do hereby declare that the following is a full, clear, and exact description of the same, reference being had to the accompanying drawings, forming part of this specification, in which—

Figure 1:
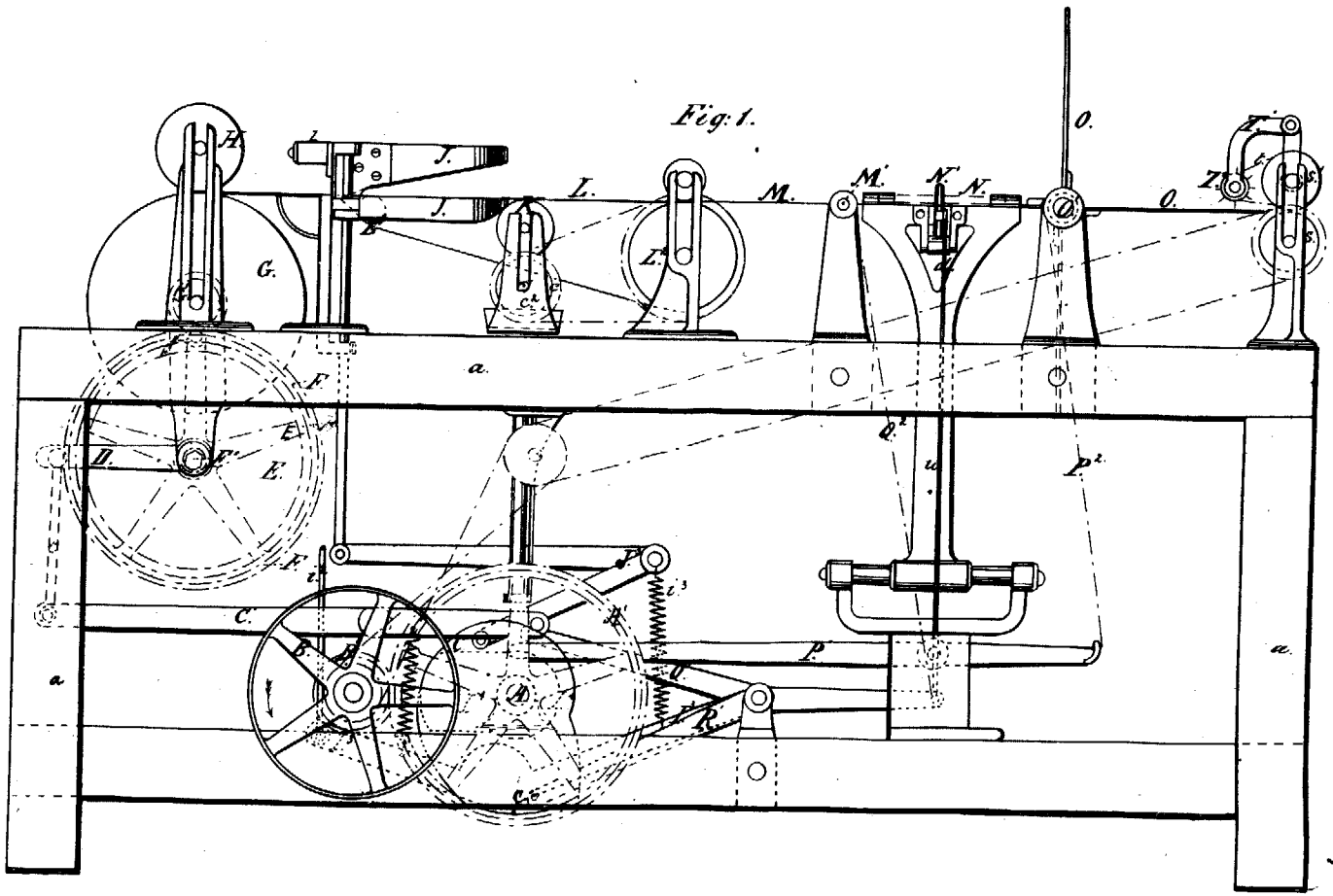
Figure 2:
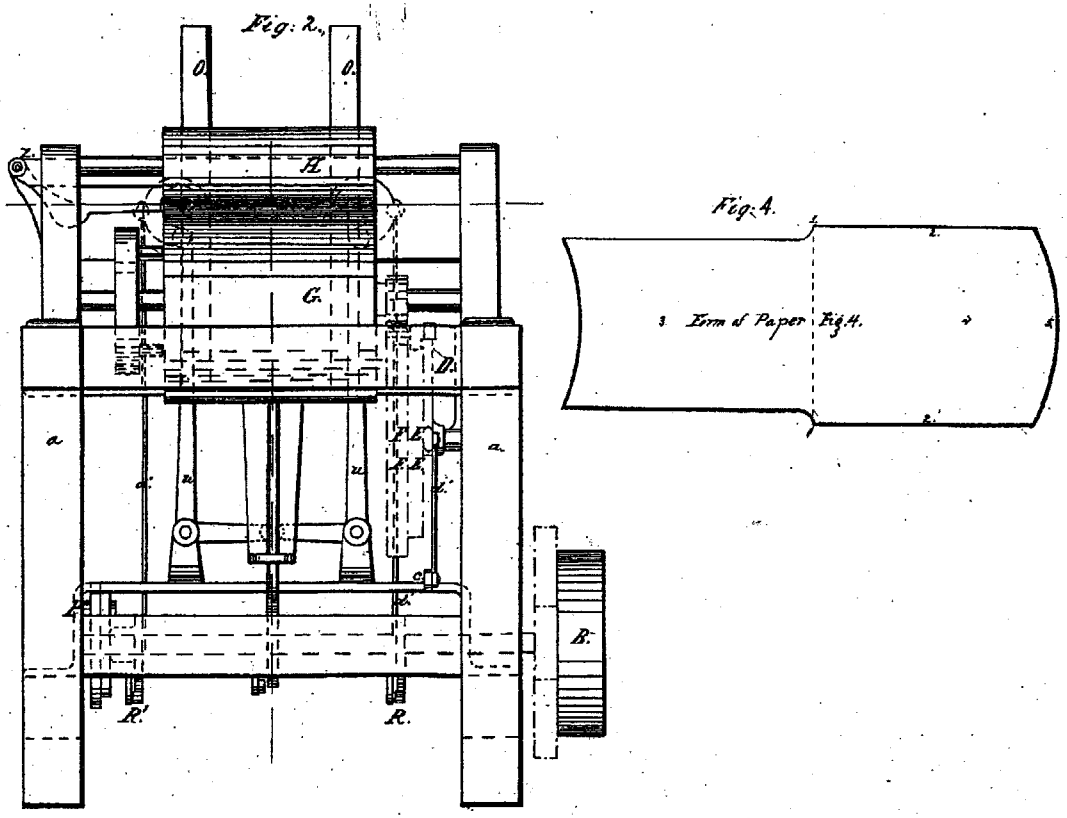
Figure 3:
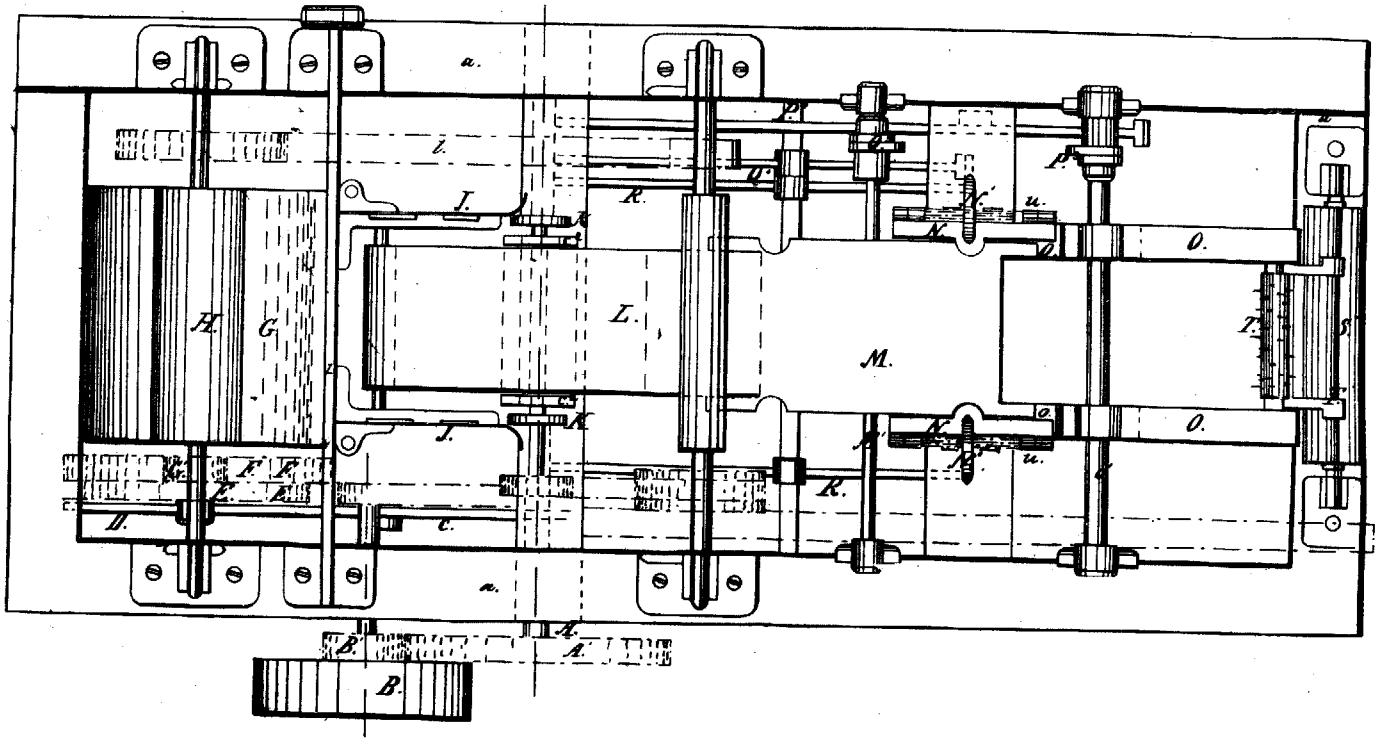
Figure 9:
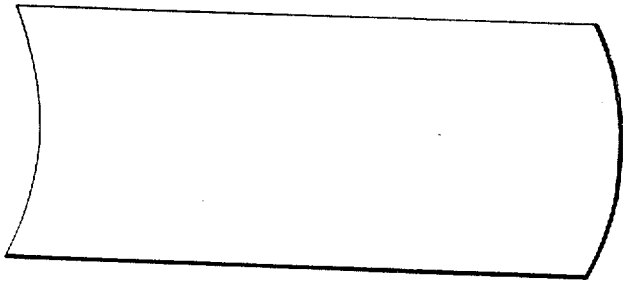
Figure 10:
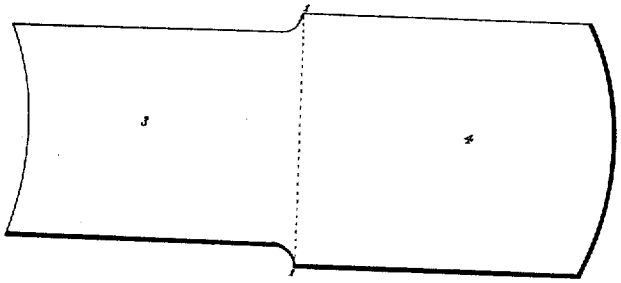
Figure 11:
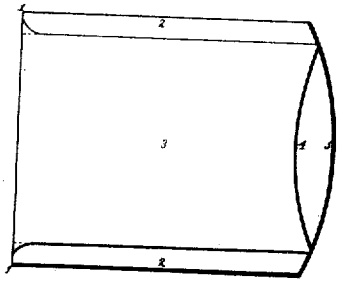
Figure 13:
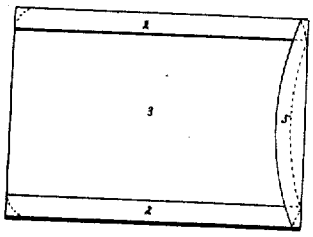
Figure 12:
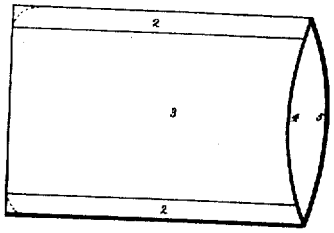

Figure 1 is a side elevation of a machine constructed according to my invention; Fig. 2, an end view of the same; Fig. 3, a plan of the same. Fig. 4 shows the shape to which the paper is cut. Fig. 5 is a longitudinal vertical section of the machine; Fig. 6, a transverse vertical section of the same in the line *x x*, Fig. 5. Fig. 7 is a detached elevation of the shears by which the paper is cut to the required shape. Fig. 8 is a plan of the same. Fig. 9 represents on a larger scale than any of the other figures the shape to which the piece of paper or other material to form the bag is cut off from a roll of uniform width. Fig. 10 represents on a similar scale to Fig. 9 the shape to which the piece is afterward cut before being folded, this figure corresponding with Fig. 4, which is on a smaller scale. Fig. 11 represents the piece partly folded. Fig. 12 represents a bag completed by the machine. Fig. 13 represents the bag with its mouth closed.

Similar letters of reference indicate corresponding parts in the several figures.

This invention consists in certain novel devices and novel arrangements and combinations of old devices constituting a machine by which paper is cut from a roll and folded, pasted, and laped to form a bag, and in a certain system of cutting the paper from the roll whereby, when a bag is completed, one side of its mouth is caused to project beyond the other in such manner as to afford facility for opening the mouth and to form a flap for closing the mouth.

To enable those skilled in the art to make and use my invention, I will proceed to describe its construction and operation.

*a a* represent the framing of the machine.

A is the main shaft, carrying a number of cams for giving motion to the different parts of the machine, and also carrying a spur-wheel, A′, gearing with a pinion, B′, attached to the driving-pulley B.

G is a feed-roll, and H a pressure-roll, the former receiving an intermittent motion to feed at proper intervals a suitable length from a roll of paper (supposed to be conveniently hung on a roll, but not shown) to form a bag, the said intermittent motion being derived from a cam, C, on the main shaft and a lever, C′, (see Fig. 1,) which is acted upon by the said cam, and connects by a rod, *c*, with one arm of a ratchet-lever, D, which carries a pawl, *c*′, engaging with a ratchet-wheel, E, which is made fast to a gear, F, which works on a fixed axle, F′, and engages with a smaller gear, G′, on the shaft of the feed-roller G.

I, Figs. 5, 7, and 8, is the stationary blade, and I′ the vibrating blade, of a pair of shears, arranged transversely in the machine for cutting off the paper to the form represented in Fig. 9 after it has been delivered by the feed-rollers on to an endless apron, L. These shear-blades are shown in Figs. 5, 7, and 8. Their cutting-edges are of such curved form as to leave a convex margin on the roll of paper and a corresponding concave margin to the piece they cut off, thus giving the two ends of every bag-piece the form shown in Figs. 4, 9, and 10.

J J are the stationary blades, and J′ J′ the movable blades, of two pairs of shears, arranged longitudinally in the machine to cut out corresponding portions of one-half of the length of each side of the bag-piece, so that when the piece is folded in the line 1 1 of Fig. 10, to bring the part 3, that is situated on one side of the line, onto the top of the part 4, that is situated on the other side of the said line, as shown in Fig. 11, the marginal portions 2 2 of the part 4 may project beyond the side edges of the part 3 to form laps, which only require to be folded over the said edges, as shown in Fig. 12, and made to adhere to the part 3 to complete the bag. The edges of the side shear-blades, J J J′ J′, are straight along the greater portion of their length, but near their extremities they are curved outward, as shown in Figs. 3 and 8, in order to cut out the sides of the bag-piece at one operation. Without such bent or curved form two pairs or sets of shears would be required on either side of the machine to cut the sides of the piece to the proper form, one arranged longitudinally and the other transversely. The said bent or curved curved form also makes the paper double at the lower corners of the bags. The stationary blades of all the shears are attached to a bridge-piece, $I^2$, standing across the frame *a a*. The shear-blade $I'$ is pivoted at one end by a pivot, *i*, in a fixed stand, $i'$, and at the opposite end is connected by a rod, $i^2$, with a lever, $I^3$, (see Fig. 1,) which is operated upon by a cam, $I^4$, on the main shaft, for the purpose of drawing down the blade to cut off the bag-piece. After the action of the cam, the lever is raised for the purpose of raising the blade by a spring, $i^3$. The blades $J'$ $J'$ are attached to vertical shafts $j'$ $j'$, (see Figs. 5, 7, and 8,) which slide up and down in guides $j^2$ $j^2$, secured to the bridge, and are connected to levers $J^3$, which are acted upon by a cam, $J^4$, on the shaft A, the action of the said cam being such as to keep the blades always raised except at the proper time for the cutting operation, when it allows them to be drawn down by a spring or springs, $J^2$, connected with the lever $J^3$, as shown in Fig. 5. In addition to the upward and downward cutting movement of the blades $J'$ $J'$, they have a slight lateral vibrating movement on the shafts $j'$ $j'$, and to produce this movement they are set slightly out of parallel with the blades J J, and are connected by a spring, $j^3$, which tends to draw them together, and while cutting to throw their edges slightly across those of J J, but their downward motion, in contact with J J, forces them gradually apart.

The above method of hanging the shear-blades is the only one I have found, after many unsuccessful experiments, to operate satisfactorily with bent blades, such as $J'$ $J'$, the operation of the bent parts of the blades being very imperfect with all other arrangements.

The endless apron L, on which the cut bag-piece represented in Figs. 4 and 10 is received, is carried by two rollers, $L'$ and $L^2$, the latter of which receives an intermittent rotary motion from the feed-roller G through a band, *l*, running over pulleys on their respective shafts, the speed of the apron corresponding with that of the periphery of the said feed-roller. While on the apron the under faces of the side margins of the part 3 of the bag-piece are pasted ready to have the lapping pieces 2 2, folded over upon them by means of two rollers, *c*, on a shaft, $c'$, working below or within the apron, the said rollers receiving a rotary motion for the purpose by a band (not shown) from the roller $L^2$. The rollers *c* are intended to take up paste from a trough or troughs below them and give it to the bag-piece, and for this purpose their shaft $c'$ is hung in a rising and falling carriage $c^2$ resting upon a cam, $c^4$, on the shaft A (see Fig. 5,) by which it is lowered and raised at suitable intervals to take up paste and give it to the paper. The paper is confined to the paste-rollers during the pasting operation by means of pressure-rollers K, which are grooved, so as only to present a number of sharp edges to the paste-roller, so that after the paper has passed the paste-roller the said pressure-roller will not take up any paste.

In close proximity to the apron L is placed an "intermittently revolving folder," indicated by M (in Figs. 1, 2, 5, and 6,) which may consist of one perfectly flat plate secured at the middle of its length to a shaft, $M'$, or of two plates, as shown in Fig. 5, parallel with each other, but a little apart, so that there is a slight step between them. The shaft $M'$ is parallel with the feed roller and rollers of the apron. The whole length of the folder is nearly equal to the length of the bag-piece, but it must be considerably narrower. The bag-piece is deposited upon the folder, while the latter is stationary in a horizontal position.

Parallel with the folder-shaft $M'$ is the intermittently revolving creaser-shaft $O'$, carrying several pairs of creasers O O, consisting of light radial arms of flat metal plate of such length and at such distance apart that each pair forms a mold upon which to fold and produce a bag.

Between the folder shaft $M'$ and the creaser-shaft $O'$ are placed two folding-stands, *d d*, which are carried by the upright arms of two elbow-levers, *u u*, (see Figs. 5 and 6,) which receive a vibrating motion to give the folding-stands a lateral movement. As soon as the piece is properly deposited on the folder, the creaser-shaft makes a portion of a revolution in the direction of the arrow shown near it in Fig. 5, and brings down a pair of creasers upon the wider part, 4, of the bag piece, and immediately after this the folder makes half a revolution in the direction of the arrow shown near it in Fig. 5, and folds the narrow part 3 over onto the wider part, 4, as shown in Fig. 11.

During the folding operation the pair of creasers which is in operation has been supported by the folding-stand *d d*, and these remain below the creasers after the folding operation and during the operation of lapping the sides, which is performed by means of lappers N N hinged to the folding stands. These lappers during the preceding operations have been thrown back to the position shown dotted in Fig. 6, and the lapping pieces 2 2 of the paper lay upon them, but as soon as the paper has been folded in the line 1 by the folder the lappers are thrown over onto the creasers, and thus lay the lapping pieces 2 2 over onto the pasted margins of the part 3, as shown in Fig. 12.

The creaser-shaft $O'$, instead of having a rotary motion, as above described, may have an alternate or reciprocating circular motion of such extent as to carry the bags from the folding-stands to the pressure and delivery rollers, by which the laps are pressed down and the bag completed, as will be presently described. In that case the above-described lateral motion of the folding-stands may be dispensed with. The movement of the folder is given at regular and proper intervals by means of a cam, Q, (see Fig. 5,) on the shaft A, acting on a lever, Q′, which draws down a cord, $Q^2$, connected with a pawl and ratchet, $Q^3$, on the folder-shaft. The return movement of the ratchet-pawl is effected by a spring, *q*, at the opposite end of the cord $Q^2$. The movement of the creaser is given in a substantially similar manner by means of a cam, P, acting on a lever, P′, which draws down a cord, $P^2$, connected with a pawl and ratchet, $P^3$, on the creaser-shaft. The return movement of this ratchet-pawl is effected by a spring, *p*. The movement of the side-lappers N N to make the laps to form the seams of the two sides of the bag is given by means of two fingers, N′ N′, which are pivoted to the elbow, levers *u u*, and connected by rods *d′ d′* with a pair of levers, R′, operated upon by cams R on the shaft *a*. The lappers are thrown back again by means of springs applied to their hinge-joints.

I have now described the manner of cutting, folding, and lapping the paper to form the bag which leaves the bag upon the creasers *o o*. All that requires to be subsequently done is to take it from the creasers and press it to insure the perfection of the seam. These operations are performed in the following manner: As soon as the side lap has been completed, the lappers N N are immediately thrown back to the position shown in dotted lines in Fig. 5, and the movement of the creaser-shaft to bring another pair of creasers into operation takes place, but previous to the movement of the creasers the folding-stands *d d* must move farther apart to allow them to pass. The movement of the stands *d d* is effected by a cam, V, on the main shaft operating upon one end of a lever, V′, at the opposite end of which is a small upright piece, $V^2$, supporting the short horizontal arms of the elbow-lever *u u*. The stands are drawn toward each other, when the cam V allows them, by means of a spring, *u′*, connecting, the upright arms of the elbow levers. Two movements of the creaser-shaft carry the bag opposite the pair of continuously-revolving pressing and delivery rollers S S′, and the removal of the bag is commenced by the sharp teeth of a roller, T, which is hung in a gate or frame, T′, swinging upon the axle of the upper roller, S′, and is driven by a small band, *t*, running from the said roller. After the bag has been drawn part of the way off the creasers, it is received between the pressing and delivery rollers S S′, and is by them pressed, and at the same time discharged from the machine in the condition represented in Fig. 12.

An important feature in the operation of this machine consists in its cutting off the paper from the roll with the edges produced by such cutting of such form that when the bag is completed and laid flat the edge of one side or half of the mouth projects in a concave form beyond the other side or half, which is of convex form, while both sides are of equal length at the corners of the mouth, as shown in Fig. 12. The bags thus made are much easier opened for filling than those which have both sides of the mouth even with each other; and, besides this, the projecting part 5 of one side constitutes a flap of a very advantageous form for closing the bag by the use of adhesive material.

What I claim as my invention, and desire to secure by Letters Patent, is—

1. Cutting off the paper from a continuous roll in a machine for making bags by a cut of such form that when a bag is completed one side of the mouth is caused by the form of the said cut to project beyond the other side, substantially as represented in Fig. 12, to afford facility for opening the bag and to form a flap for closing the mouth.

2. Giving the blades of the side shears, J J′, J J′, a curved angular or irregular form near the point, for the purpose of cutting out, each by a single cut, the whole piece necessary to leave the lap on one side of the bag, substantially as represented in Figs. 4 and 10.

3. Hanging the movable blades J′ J′ of the said shears on shafts or pivots *j j* perpendicular to their faces for the purpose of allowing them to cut slightly across the fixed blades by a slight lateral movement, which they receive simultaneously with the movement usually given to shears, substantially as described.

4. The intermittently-rotating folder, arranged and operating substantially as described, to receive the bag-pieces from the feed-apron L after the cutting and pasting operations, and to support or partly support them until the creasers come into their operative positions and afterward to fold them over the creasers.

5. The combination of the side-lappers N N and the folding-stands *d d*, substantially as described—that is to say, the stands being so placed as to support the bag-piece and the creasers during the folding and lapping operations and to allow the folder to pass between them, and the lapping pieces being attached to the said folding-stands in such a manner as to be capable of falling over those creasers which are supported by the folding-stands; this I claim irrespective of any manner of operating the lappers and whether the folding-stands have the lateral movement described or are stationary.

6. The toothed roller T, hung in a frame, T′, from the axle of one of the pressing and delivery rollers, and operating, substantially as described, to commence the removal of the bags from the creasers.

7. The general arrangement and combination of the several working parts of the machine, substantially as herein described.

E. W. GOODALE.

Witnesses:
EZRA SAWYER,
H. T. GOODALE.